US006993406B1

(12) United States Patent
Cesarano, III et al.

(10) Patent No.: US 6,993,406 B1
(45) Date of Patent: Jan. 31, 2006

(54) METHOD FOR MAKING A BIO-COMPATIBLE SCAFFOLD

(75) Inventors: Joseph Cesarano, III, Albuquerque, NM (US); John N. Stuecker, Albuquerque, NM (US); Jennifer G. Dellinger, Champaigne, IL (US); Russell D. Jamison, Urbana, IL (US)

(73) Assignee: Sandia Corporation, Albuquerque, NM (US)

( * ) Notice: Subject to any disclaimer, the term of this patent is extended or adjusted under 35 U.S.C. 154(b) by 0 days.

(21) Appl. No.: 10/831,735

(22) Filed: Apr. 23, 2004

Related U.S. Application Data

(60) Provisional application No. 60/465,904, filed on Apr. 24, 2003.

(51) Int. Cl.
*A61F 2/28* (2006.01)
*A61F 2/00* (2006.01)
(52) U.S. Cl. .................... 700/119; 700/118; 623/23.75; 424/422; 424/428; 424/423; 425/375
(58) Field of Classification Search ................ 700/119, 700/118; 623/23.75; 424/422, 428, 423; 425/375
See application file for complete search history.

(56) References Cited

U.S. PATENT DOCUMENTS 4,599,085 A     7/1986  Riess et al.

| 4,626,392 A |   | 12/1986 | Kondo et al. |
|---|---|---|---|
| 4,737,411 A | * | 4/1988 | Graves et al. ............. 428/403 |
| 5,306,673 A |   | 4/1994 | Hermansson et al. |
| 5,370,692 A | * | 12/1994 | Fink et al. .................. 128/898 |
| 5,490,962 A |   | 2/1996 | Cima et al. |
| 5,587,913 A | * | 12/1996 | Abrams et al. ............. 700/119 |

(Continued)

OTHER PUBLICATIONS

"Robocasting: Joe Cesarano developes breakthrough way of fabricating ceramics" -Chris Burroughs, Sandia National Labratories- Jan. 29, 1999.*

(Continued)

*Primary Examiner*—Albert W. Paladini
*Assistant Examiner*—Michael D. Masinick
(74) *Attorney, Agent, or Firm*—Elmer A. Klavetter

(57) ABSTRACT

A method for forming a three-dimensional, biocompatible, porous scaffold structure using a solid freeform fabrication technique (referred to herein as robocasting) that can be used as a medical implant into a living organism, such as a human or other mammal. Imaging technology and analysis is first used to determine the three-dimensional design required for the medical implant, such as a bone implant or graft, fashioned as a three-dimensional, biocompatible scaffold structure. The robocasting technique is used to either directly produce the three-dimensional, porous scaffold structure or to produce an over-sized three-dimensional, porous scaffold lattice which can be machined to produce the designed three-dimensional, porous scaffold structure for implantation.

17 Claims, 2 Drawing Sheets

FCC

SC

Modified FCC non-periodic

U.S. PATENT DOCUMENTS

| | | | |
|---|---|---|---|
| 6,017,508 A * | 1/2000 | Millar et al. | 423/700 |
| 6,027,326 A | 2/2000 | Cesarano et al. | |
| 6,103,255 A | 8/2000 | Levene et al. | |
| 6,139,574 A | 10/2000 | Vacanti | |
| 6,311,095 B1 * | 10/2001 | Brown | 700/117 |
| 6,324,438 B1 * | 11/2001 | Cormier et al. | 700/118 |
| 6,346,123 B1 | 2/2002 | McKay | |
| 6,479,418 B2 | 11/2002 | Li et al. | |
| 6,527,810 B2 | 3/2003 | Johnson et al. | |
| 6,530,956 B1 * | 3/2003 | Mansmann | 623/18.11 |
| 6,626,950 B2 | 9/2003 | Brown et al. | |
| 6,630,153 B2 | 10/2003 | Long et al. | |
| 6,642,285 B1 * | 11/2003 | Bohner | 523/115 |
| 6,692,761 B2 | 2/2004 | Mahmood et al. | |
| 6,772,026 B2 * | 8/2004 | Bradbury et al. | 700/98 |
| 2002/0160175 A1 * | 10/2002 | Pirhonen | 428/297.4 |

OTHER PUBLICATIONS

"Growing Bones in the Lab" -Margret Lovell, TechComm, Oct. 2004.*

Stuecker, Ind. Eng. Chem. Res. 2004, 43, p. 51-55.

* cited by examiner

METHOD FOR MAKING A BIO-COMPATIBLE SCAFFOLD

This application claims the benefit of U.S. Provisional Application No. 60/465,904, filed on Apr. 24, 2003.

This invention was made with Government support under Contract No. DE-AC04-94AL85000 awarded by the Department of Energy. The Government has certain rights in the invention.

BACKGROUND OF THE INVENTION

The invention describes a method for forming a three-dimensional (3D) scaffold structure bio-compatible for use as a medical implant and, more specifically, for forming, using a rapid-prototyping method, a 3D scaffold structure that can be implanted in a living body as replacement for bone and for promoting bone growth.

Bone graft is used to fill spaces in bone tissue that are the result of trauma. Clinicians perform bone graft procedures for several reasons, often to fill a bone void created by a loss of bone due to trauma, degeneration due to disease or other loss of tissue. In many instances, the clinician also must rely on the bone graft material to provide some mechanical support, as in the case of subchondral bone replacement or compaction grafting around total joint replacement devices. In these instances, clinicians pack the material into the defect to create a stable platform to support the surrounding tissue and hardware. Additionally, the clinician may rely on the material to facilitate cell growth and extracellular matrix production.

There are several options available to the orthopedic clinician for bone graft material, including autografts (bone from the patient), allografts (cadaver bone), and a variety of artificial or synthetic bone substitute materials. Autografts are comprised of cancellous bone and cortical bone. Cancellous bone grafts provide virtually no structural integrity. Bone strength increases as the graft is incorporated and new bone is laid down. For cortical bone, the graft initially provides some structural strength. However, as the graft is incorporated by the host bone, nonviable bone in the graft is removed by osteoclast resorption, reducing the strength of the graft. The use of autograft bone may result in severe patient pain at the harvest site, and there is, of course, a limit to the amount of such bone that can be harvested from the patient. Allografts are similar to autografts in that they are comprised of cancellous and/or cortical bone with greater quantities and sizes being available. Sterilization techniques for allografts may compromise the structural and biochemical properties of the graft. The use of allograft bone bears at least some risk of transfer of disease and the risk that the graft may not be well incorporated.

Synthetically derived bone graft substitutes have advantages over human derived bone grafts and naturally derived substitutes, including: 1) more control over product consistency; 2) less risk for infection and disease; 3) no morbidity or pain caused by harvesting of the patient's own bone for graft; and 4) availability of the substitute in many different volumes (that is, it is not limited by harvest site of the patient). The bone graft materials that have been used commercially exhibit various levels of bioactivity and various rates of dissolution. These materials are currently available in several forms: powders, gels, slurry/putties, tablets, chips, morsels, and pellets, in addition to shaped products (sheets, and blocks). In many instances, the form of bone graft products is dictated by the material from which they are made. Synthetic materials (such as calcium sulfates or calcium phosphates) have been processed into several shapes (tablets, beads, pellets, sheets, and blocks) and may contain additives such as antibiotics or bioactive agents. Allograft products, in which the source of the bone graft material is a donor, are typically available as chips and can be mixed with a gel to form a composite gel or putty. None of the current bone graft products and technologies is capable of offering an allograft with a scaffold structure, nor does it match the size and shape of the surgical defect. Furthermore, none but one of the current products and technologies offered for bone graft materials is capable of offering an allograft or synthetic granule or shape containing a bioactive agent or agents, such as an antibiotic or bone morphogenetic proteins.

For structural bone repair materials to be conveniently used, they must be capable of being formed into complex shapes that are designed to fit the contours of the repair site. An accurately contoured graft will enhance the integration of natural bone and provide better load carrying capability. Intimate, load carrying contact often is required between the natural bone and the bone substitute material to promote bone ingrowth, remodeling, and regeneration, leading to incorporation of the graft by host bone. Ideally, the strength, stiffness, and resilience (that is, its response to load and rate of load) of the bone substitute material should be similar to that of natural bone. Ideal mechanical properties of any scaffold will vary depending on the clinical application because the elastic modulus of bone differs according to anatomical location.

Many materials have been proposed for use as bone substitute materials, ranging from shaped porous metal objects suitable for defect filling around knee and hip joint replacements on the one hand to shaped ceramic materials on the other. Ceramic materials by and large have been formed through a sintering process in which a powder of a ceramic material such as zirconia is compressed to a desired shape in a mold and is then heated to sintering temperatures. The porosity of the resulting material is commonly quite low unless a porogen is added to the powder before molding. Materials employing calcium phosphates (for example: fluorapatite, hydroxyapatite, and tricalcium phosphate) can also be sintered in this manner; the hydroxyapatite and the tricalcium phosphate having the capacity for acting as a substrate for bone growth (osteoconductivity).

Metal or ceramic materials that have been proposed for bone substitutes have been of low porosity and have involved substantially dense metals and ceramics with semi-porous surfaces filled or coated with a calcium phosphate based material. The resulting structure has a dense metal or ceramic core and a surface which is a composite of the core material and a calcium phosphate, or a surface which is essentially a calcium phosphate. The bone substitute materials of this type commonly are heavy and dense, and often are significantly stiffer in structure than bone. Whereas natural bone, when stressed in compression, fails gradually (some components of the bone serving to distribute the load), bone substitute materials such as those described above commonly fail suddenly and catastrophically.

Porous ceramic materials such as hydroxyapatite and soluble glasses have also been used as scaffolds for the ingrowth of tissue due to compositional and morphological biocompatability. For example, the porosity of such materials promotes cell infiltration. A variety of methods are used to prepare porous ceramic scaffolds (prostheses), such as hydrothermally treating animal bone or coral, burning off polymer beads mixed into a ceramic body, vapor deposition on foam, infiltration of polymer foam with a ceramic slip and foaming a ceramic slip.

One limitation exhibited by porous ceramic materials is their inherent brittleness. Attempts to address this limitation have included back-filling a ceramic foam with monomer solutions of PMMA or PLA, draining excess solution from the ceramic foam then polymerizing through curing and/or drying in order to impart some toughness to the ceramic foam. Others have proposed laminating solid or porous polymeric layers to a ceramic foam structure.

Independent from proposed uses in combination with ceramics, polymeric foams have utility in the repair and regeneration of tissue. For example, amorphous, polymeric foam has been used to fill voids in bone. Various methods have been explored for preparing the polymer foams, using, e.g., leachables; vacuum foaming techniques; precipitated polymer gel masses; and polymer melts with fugitive compounds that sublime at temperatures greater than room temperature. Additionally, some methods allow the incorporation of thermally sensitive compounds like proteins, drugs, and other additives. These materials however lack the structural integrity required for use as scaffolds for some medical applications.

In the case of fracture or other injury to bone, proper bone healing and favorable bone remodeling is highly dependent on maintaining stability between bone fragments and on maintaining physiologic strain levels. External structural support can be gained using external braces, casts and the like. Internal structural support commonly is supplied by internal fixation devices such as bone plates, screws, and intermedullary rods, some of which may need to be surgically removed and all of which may prove to be burdensome and traumatic to a patient.

There is thus a need for a product that is a bone substitute material and that also provides structural support. This is especially so in the replacement or repair of long bones of the lower extremities and for use in spinal fusion techniques. Trauma, osteoporosis, severe osteoarthritis or rheumatoid arthritis, joint replacement, and bone cancers may call for treatment involving the use of structural bone substitute materials. A successful bone graft requires an osteoconductive matrix providing a scaffold for bone ingrowth, osteoinductive factors providing chemical agents that induce bone regeneration and repair, osteogenic cells providing the basic building blocks for bone regeneration by their ability to differentiate into osteoblasts and osteoclasts, and structural integrity provided to the graft site suitable for the loads to be carried by the graft. Tissue regeneration devices must be porous with interconnected pores to allow cell and tissue penetration. Factors such as pore size, shape, and tortuosity can all affect tissue ingrowth. Needed are methods to construct intricate three-dimensional structures from biocompatible materials with controllable pore structure and suitable mechanical strength and fluid transport characteristics.

BRIEF DESCRIPTIONS OF THE DRAWINGS

DESCRIPTION OF SPECIFIC EMBODIMENTS

Figure 1:
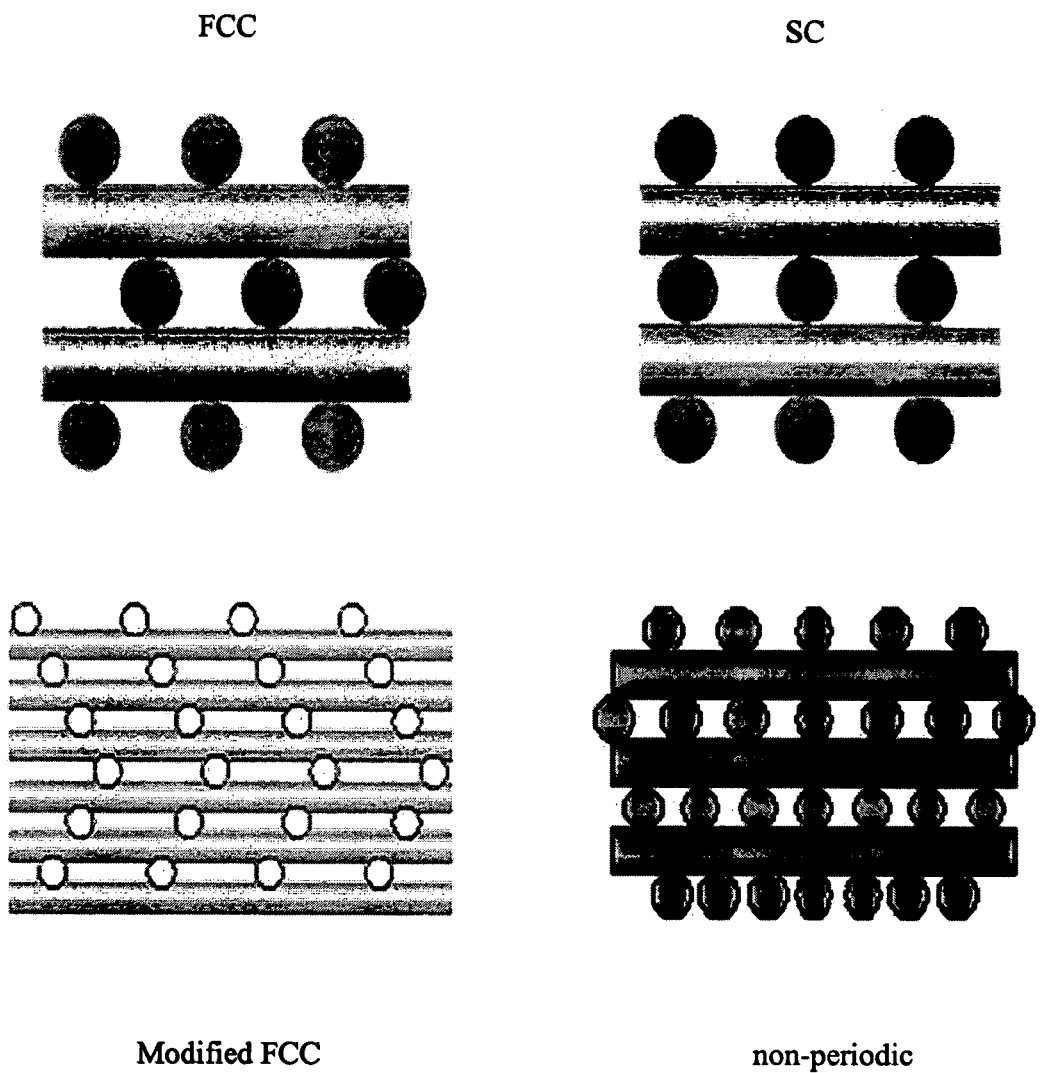
FIG. 1 shows illustrative three-dimensional geometries of robocast scaffolds that can be utilized in the method of the present invention.

Hydroxyapatite (HA), $Ca_{10}(PO_4)_6(OH)_2$, is a calcium phosphate ceramic commonly used for bone tissue repair in non-load bearing applications. Because bone cannot restore itself if a critical size defect is present, a porous scaffold to which cells can attach and proliferate is needed to fill and reconstruct the defect. As cells infiltrate the scaffold and proliferate, the scaffold degrades, freeing more space for continued cell growth and tissue formation. Eventually, the scaffolds are partially resorbed and incorporated into adjacent and remodeled bone.

Bone defects caused by trauma or disease may require repair via surgical intervention. In surgery, defects are filled with natural or synthetic grafts to inhibit fibrous tissue formation and to promote the ingrowth of bone tissue into the defect. Bone ingrowth is encouraged by scaffolds which are fabricated from biocompatible, osteoconductive materials, such as calcium phosphates. Hydroxyapatite (HA), a calcium phosphate, is an attractive material for bone applications when used to fabricate scaffolds or to coat implants such as titanium hip stems. For example, the addition of HA coatings on titanium promotes bone formation over titanium alone.

In addition to implant material, the surface topography of an implant plays a critical role in the bone cell response in vitro and in vivo. Osteoblast proliferation and matrix production in vitro has been shown to be affected by the surface topography of titanium. When titanium hip stems are implanted in vivo, surface topography affects the attachment rate and strength of the bone-implant bond. Smooth surfaces of titanium induce fibrous tissue, whereas rough surfaces induce bone formation. The type of tissue formation affects both the regenerated tissue quality and the strength of the tissue-implant bond. The strength of tissue-implant bond plays a major role in the clinical success of the implant.

Surface topography is typically produced by line of sight methods, such as plasma spraying onto and grit blasting of titanium implants or by polishing of ceramics. These methods are not applicable for creating topography on all surfaces of scaffolds, especially the surfaces of pores at the center of scaffolds. In order to create surface topography on HA scaffolds, techniques such as the addition of polymer fugitive porogen microspheres which burn out during processing and controlled sintering can be utilized. These pores cause changes in surface topography and may thereby affect cell-surface interactions that in turn mediate cell attachment, proliferation, spreading, differentiation, and function.

In vivo degradation of HA occurs by dissolution in aqueous body fluids, resorption by osteoclasts and multinuclear cells, and phagocytosis of particles by macrophages. As HA scaffolds degrade, strength is progressively lost. For load bearing applications, ingrown bone tissue must provide compensating strength in order to support mechanical load at the site of implantation. Eventually, the remodeled bone bears more load as the scaffold is slowly resorbed. As bone heals, the mechanical properties of the scaffold should decrease commensurately to accommodate the increasing strength provided by the ingrown bone. Bone subjected to increased load remodels and strengthens to accommodate such load. The inverse applies for decreased loads. Because proper bone repair requires load-bearing during the healing period, the porous, degrading scaffold must deform similarly to healthy bone under a given load, i.e. the implant must have an elastic modulus similar to that of bone. Scaffolds that provide too much or too little support for the bone may actually discourage new cell growth and consequently lengthen the healing process. Ideal mechanical properties of any scaffold will vary depending on the clinical application because the elastic modulus of bone differs according to anatomical location.

Microporous scaffolds dissolve more quickly than non-microporous scaffolds. The difference in dissolution rate is attributed to the surface area to volume ratio of the scaffolds. These differences allow for the tailorability of scaffold mechanical properties. A combination of microporous and non-microporous scaffolds would produce a scaffold with mechanical properties that match the properties of natural bone more closely. Such scaffolds possessing regions with and without local porosity formed by porogens could be produced by a solid freeform fabrication technique referred to herein as robocasting because multiple materials can be deposited in the same sample. In addition, scaffold mechanical properties can be tailored using the robocasting technique by altering the pore size, shape, and alignment. Scaffolds containing regions with and without local porosity formed by porogens have the potential to for a wide variety of load-bearing applications because the elastic modulus of bone differs by anatomical location.

Figure 2:
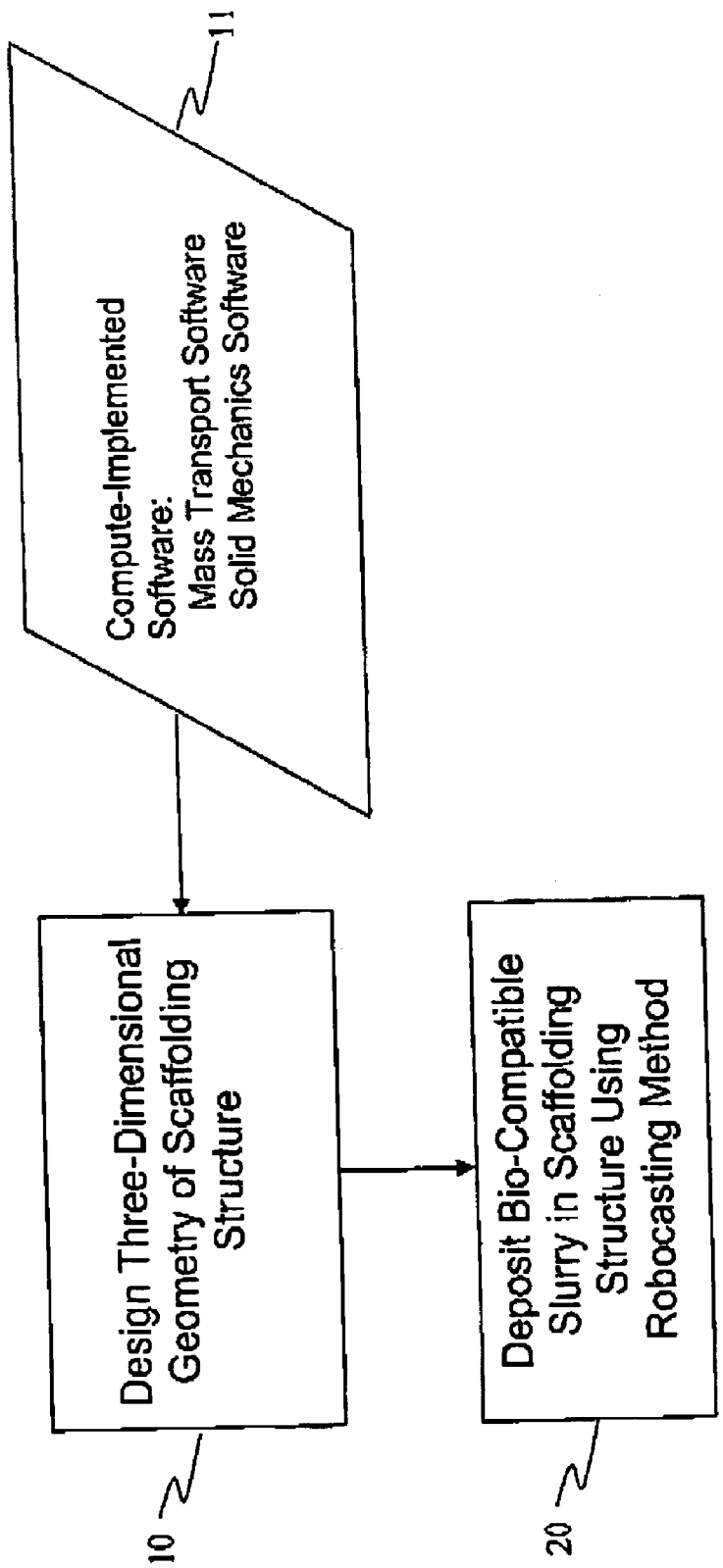
FIG. 2 illustrates the method of the present invention.

In the present invention, a three-dimensional, biocompatible, porous scaffold structure, with examples of such structures illustrated in FIG. 1, is formed using robocasting that can be used as a medical implant into a living organism, such as a human or other mammal. Depicted in FIG. 1 are structures that represent a face-centered cubic (FCC) geometry, a simple cubic (SC) geometry, a modified FCC geometry, and a non-periodic geometry with individual elements. As shown in the flow-chart of FIG. 2, imaging technology and analysis, using computer implemented software 11 that can include mass transport software and solid mechanics software, are first used to determine the three-dimensional design 10 required for the medical implant, such as a bone implant or graft, fashioned as a three-dimensional, biocompatible scaffold structure. The robocasting technique 20 (although other rapid prototyping methods can be used) is used to either directly produce the three-dimensional, porous scaffold structure or to produce an over-sized three-dimensional, porous scaffold lattice which can be machined to produce the designed three-dimensional, porous scaffold structure for implantation.

One important feature of using the robocasting technique is the capability to produce controllable porosity on multiple scale levels, resulting in a scaffold structure with macroporosity (spacings ranging from greater than 50 microns to more than 1000 microns), microporosity (pore size diameters ranging from approximately 1 to 50 microns) and nanoporosity (comprising the porosity between grain boundaries of the materials used with diameters less than 1.0 microns). By controlling the material used, the pore structure and the sizes of the individual elements used to construct the three-dimensional scaffold structure, the strength of the scaffold structure can also be controlled, with compressive modulus values of greater than 5 GPa and compressive strength values from approximately 25 MPa to greater than 300 MPa achievable. The mechanical properties of the scaffold can thus be matched to the properties required of the implant; for example, the properties of a bone graft for a cortical bone (compressive modulus of 7–27 GPa and compressive strength of 85–224 MPa) can thus be matched.

Robocasting is a moldless-fabrication, rapid-prototyping technique, generally automated, for extruding concentrated particulate pastes, described by Cesarano III et al., (U.S. Pat. No. 6,027,326; incorporated by reference herein). The technique can be used in the formation of three-dimensional structures, including self-supporting lattice structures, from materials in a variety of shapes. Materials that can be used include, but are not limited to, ceramics, such as alumina, mullite, zirconia, silicon carbide, silicon nitride, zinc oxide, barium titanate, barium strontium titanate, lead zirconate titanate (PZT), kaolin, hydroxyapatite, hexaaluminates; metals, such as tungsten, silver, molybdenum, and stainless steel; polymers, thick-film pastes, epoxies, sol-gel materials, and composites, such as $Al_2O_3$/TiCuSil, $Al_2O_3$/Al, $Al_2O_3$/Mo, zirconia/mullite, porous/dense PZT materials, porous/dense alumina, and PZT/polymer materials.

In the robocasting process, highly concentrated slurries (suspensions) containing a powder (from a ceramic, metal, glass, polymer or composite material), with particle sizes generally around 1 micron in diameter, and solvent (generally water) are deposited, or 'written' in a layer-wise fashion with discrete or individual elements, with the process generally automated and computer controlled. The process is conceptually similar to icing a cake, with two-dimensional layers of the suspension material being sequentially deposited, and then writing subsequent layers in a rapid fashion to produce three-dimensional objects of high complexity. The highly concentrated suspensions generally contain very low amounts of organic material, allowing for prompt curing and final sintering of the part in a rapid-prototyping manner. Modifications to the robocasting process have shown that the technique can also be employed in a rapid-manufacturing environment. Controlling the viscous behavior of the suspension to a paste-like consistency enables shape retention of the deposited lines (in the form of cylindrical rods or other geometric shapes) of material until drying has taken place and also allows distances to be spanned. Proper adjustment of the ceramic suspension viscosity allows for the creation of self-supporting lattices or scaffolds. The mechanical properties of the scaffold structure can be tailored based on the physical and compositional characteristics of the individual shape elements and the geometry of those elements. Additionally, tortuosity and porosity of fluid flow paths can be tailored, based on design requirements, from straight-through pathways found in traditional honeycomb extrudates to pathways with no direct line-of-sight. These characteristics can prove important in enhancing cell growth in some situations. The geometry of the three-dimensional structure itself can also be controlled.

Examples of various three-dimensional frameworks or structures that can serve as the geometry of the scaffold structure, utilizing a sequence of cylindrical geometric constructs, are shown in FIG. 1. Depicted are structures that represent a face-centered cubic (FCC) geometry, a simple cubic (SC) geometry, a modified FCC geometry, and a non-periodic geometry with individual elements (in this case, cylindrical constructs, although other polyhedral geometrical constructs can be used, including those with rectangular, rhombic, trapezoidal, triangular or variable cross-sectional geometries,) comprising the three-dimensional structure of variable dimensions (diameters). The placement of these cylindrical constructs (rods) can be tailored to control both mechanical and fluid flow properties, based on design requirements. Sizes of the discrete elements used in the structure can vary within the structure but generally have characteristic dimensions ranging from approximately 0.05 mm to greater than 3 mm. For medical applications, the structures generally have sizes ranging from approximately 1 mm to greater than 200 mm, although larger structures can be fabricated if the application warrants.

In one example, a situation existed where it was desirable to fabricate and insert a scaffold structure into a severely deteriorated mandible. Imaging analysis was performed by taking a computerized axial tomographic (CAT) scan of the mandible area and using software to determine the three-dimensional geometry needed for a synthetic bone implant.

Software was used to design a solid computer model of the implant. Robocasting was used to fabricate a three-dimensional, porous lattice structure comprising hydroxyapatite with size dimensions exceeding that of the desired bone implant. The fabricated lattice structure had a modified FCC structure using cylindrical rod elements with a macroporosity of approximately 50% based on the volume of the three-dimensional structure (with individual elements having spacings of 300–500 $\mu$m), a microporosity (based on the total volume of the individual elements) of approximately 30% (with pore sizes of approximately 6–10 $\mu$m), and a nanoporosity (based on the total volume of the individual elements) of approximately 10% (with pore sizes of approximately 0.5 $\mu$m). Using other geometries and materials, the macroporosity can range from 0–80%, the microporosity can range from 0–70%, and the nanoporosity can range from 0–60% (again, with the porosity of the latter two based on the volume of the individual elements) The fabricated structure had a compressive modulus of approximately 3.3 GPa and a compressive strength of approximately 137 MPa. The fabricated structure was machined using standard techniques to match the computer-developed solid model of the bone implant. The bone implant was then implanted into the deteriorated mandible using standard medical implant techniques.

Three-dimensional, porous biocompatible structures can also be fabricated according to the method of the present invention for the primary purpose of controlled drug dispersal within the living organism. Because the method of the present invention allows controlled tailoring of the pore structure of the implant on the macropore, micropore, and nanopore level, permitting control of fluid flow characteristics, implants can be fabricated that incorporate bioactive agents. There are essentially no limitations on the bioactive agents that can be incorporated into an implant using the method of the present invention, as the bioactive materials can either be incorporated directly into the slurry that forms the three-dimensional, porous structure or can be dispersed within the porosity of the three-dimensional porous structure. In the latter case, the bioactive agent can be contained within the porous structure either through physical or chemical means.

Examples of bioactive agents that can be used include growth factors, other proteins and peptides, nucleic acids, polysaccharides, nucleic acids, lipids, and non-protein organic and inorganic compounds. These bioactive agents can have biological effects including, but not limited to, anti-inflammatories, antimicrobials, anti-cancer, antivirals, hormones, antioxidants, channel blockers, and vaccines. It is also possible to incorporate materials not exerting biological effects such as radiopaque materials and other imaging agents.

When these bioactive agents are incorporated into the porosity of the structure and implanted into the living agent, they can be released into the agent either through mass transport through the structure or can be released as the structure erodes. The release rate can thus be controlled through proper design of the porous structure and a priori analysis of the transport properties of the bioactive agent and the erosion properties of the structure. Concentration variations of the bioactive agent can be intentionally incorporated into the implanted structure. Additionally, variations in erosion properties can be incorporated into the structure through control of material properties as well as geometric properties of the structure.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for making a three-dimensional, bio-compatible scaffold structure, comprising:
    designing a three-dimensional geometry of a scaffolding structure utilizing software implemented by a computer;
    said software selected from the group consisting of mass transport software and solid mechanics software to match a pre-selected property, said property selected from the group consisting of compressive modulus, compressive strength, porosity of the porous structure, tortuosity of the porous structure, and mass transport characteristics of the porous structure; and
    depositing a bio-compatible slurry as discrete elements in said three-dimensional geometry using a robocasting rapid-prototyping method to construct a three-dimensional, porous structure, said three-dimensional porous structure comprising macroporosity between approximately 0 and 80%, microporosity of said discrete elements between 0 and 70% and nanoporosity of said discrete elements between approximately 0 and 60%.

2. The method of claim 1 wherein said three-dimensional porous structure is selected from a face-centered cubic structure, a simple cubic structure, a modified face-centered cubic structure, and a non-periodic structure.

3. The method of claim 1 wherein said slurry comprises a powder and a solvent, said powder selected from a ceramic, a metal, a glass, a polymer, and a composite material.

4. The method of claim 3 wherein said powder is selected from a material selected from alumina, mullite, zirconia, silicon carbide, silicon nitride, zinc oxide, barium titanate, barium strontium titanate, lead zirconate titanate, kaolin, a hydroxyapatite, a hexaaluminate, tungsten, silver, molybdenum, stainless steel, thick-film pastes, epoxies, sol-gel materials, $Al_2O_3$/TiCuSil, $Al_2O_3$/Al, $Al_2O_3$/Mo, zirconia/mullite, a porous/dense lead zirconate titanate material, porous/dense alumina, and a lead-zirconate-titanate/polymer material.

5. The method of claim 4 wherein said solvent is water.

6. The method of claim 3 wherein the slurry additionally comprises an organic material to assist in characteristics selected from the curing rate, the drying rate and the mechanical properties.

7. The method of claim 1 wherein said three-dimensional porous structure has a compressive strength greater than 25 MPa.

8. The method of claim 1 wherein said three-dimensional porous structure has a compressive modulus greater than 5 GPa.

9. The method of claim 1 wherein said three-dimensional porous structure comprises at least two individual elements, said individual elements each having a geometry selected from a polyhedral geometry and a cylindrical rod geometry.

10. The method of claim 9 wherein said individual elements have at least one geometry selected from a cylindrical rod, and polyhedral geometrical constructs with a cross-sectional geometry selected from rectangular, rhombic, trapezoidal, triangular and variable cross-sectional geometries.

11. The method of claim 10 wherein said individual elements have a characteristic dimension between 0.05 mm and 3.0 mm.

12. The method of claim 1 wherein said three-dimensional porous structure has a characteristic length dimension from less than 1 mm to greater than 200 mm.

13. The method of claim 10 wherein said individual elements have variable compositions.

14. The method of claim 3 wherein the slurry additionally comprises a dopant of variable concentration in said slurry.

15. The method of claim 1 wherein said three-dimensional porous structure is further machined to produce an implantable structure.

16. The method of claim 1 wherein the discrete elements have a spacing between 0 and 1000 microns and pores with a diameter between 1 and approximately 10 microns.

17. A method for making a three-dimensional, biocompatible scaffold structure, comprising:

designing, using imaging analysis utilizing software implemented by a computer, a three-dimensional geometry of a scaffolding structure;

said software selected from the group consisting of mass transport software and solid mechanics software to match a pre-selected property, said property selected from the group consisting of compressive modulus, compressive strength, porosity of the porous structure, tortuosity of the porous structure, and mass transport characterstics of the porous structure; and depositing a biocompatible material as discrete elements in said three-dimensional geometry using a rapid-prototyping method to construct a three-dimensional, porous structure, said three-dimensional porous structure comprising macroporosity between approximately 0 and 80%, microporosity of said discrete elements between 0 and 70% and nanoporosity of said discrete elements between approximately 0 and 60%, said discrete elements having a spacing ranging between 300 microns to 1000 microns, said discrete elements having pores with diameters between 1 and 10 microns.

* * * * *